US005611772A

United States Patent [19]
Fujimoto et al.

[11] Patent Number: 5,611,772
[45] Date of Patent: Mar. 18, 1997

[54] AIR MASSAGE DEVICE

[75] Inventors: Shinichiro Fujimoto; Yoshikiyo Yamasaki, both of Osaka-fu, Japan

[73] Assignees: Kabushiki Kaisha Fuji Iryoki; Kabushiki Kaisha Japan Health, both of Osaka-fu, Japan

[21] Appl. No.: 422,502

[22] Filed: Apr. 12, 1995

Related U.S. Application Data

[63] Continuation-in-part of Ser. No. 212,957, Mar. 15, 1994, abandoned, Ser. No. 212,956, Mar. 15, 1994, abandoned, and Ser. No. 212,959, Mar. 15, 1994, abandoned.

[51] Int. Cl.[6] .................................................. A61H 7/00
[52] U.S. Cl. ........................................ 601/149; 601/150
[58] Field of Search ............................. 601/148–150, 601/84, 107

[56] References Cited

U.S. PATENT DOCUMENTS

| | | | |
|---|---|---|---|
| 1,772,310 | 8/1930 | Hart | 601/148 |
| 2,245,909 | 6/1941 | Enfiajian | 601/148 |
| 3,492,988 | 2/1970 | DeMare | 601/148 |
| 3,653,083 | 4/1972 | Lapidus | 601/148 |
| 3,760,801 | 9/1973 | Borgeas | 601/148 |
| 3,778,851 | 12/1973 | Howorth | 601/148 |
| 4,197,837 | 4/1980 | Tringali et al. | 601/150 |
| 4,225,989 | 10/1980 | Corbett et al. | 601/148 X |
| 4,267,611 | 5/1981 | Agulnick | 601/148 X |
| 4,347,633 | 9/1982 | Gammons | 601/148 |
| 4,583,255 | 4/1986 | Mogaki et al. | 601/150 X |
| 4,622,706 | 11/1986 | Takeuchi | 601/148 |
| 4,890,344 | 1/1990 | Walker | 5/453 |
| 5,010,608 | 4/1991 | Barnett | 5/453 |
| 5,029,939 | 7/1991 | Smith | 601/148 |
| 5,103,518 | 4/1992 | Gilioy et al. | 5/453 X |
| 5,135,282 | 8/1992 | Pappers | 601/148 X |
| 5,211,162 | 5/1993 | Gillen | 601/149 |
| 5,233,974 | 8/1993 | Senoue | 601/149 |
| 5,394,577 | 3/1995 | James et al. | 5/455 |

FOREIGN PATENT DOCUMENTS

| | | | |
|---|---|---|---|
| 3-10994 | 3/1991 | Japan . | |
| 404266757 | 9/1992 | Japan | 601/149 |
| 405345004 | 12/1993 | Japan | 601/148 |
| 405345005 | 12/1993 | Japan | 601/148 |
| 6-1948 | 1/1994 | Japan . | |
| 6-1960 | 1/1994 | Japan . | |

*Primary Examiner*—Robert A. Hafer
*Assistant Examiner*—Brian E. Hanlon
*Attorney, Agent, or Firm*—Flynn, Thiel, Boutell & Tanis, P.C.

[57] ABSTRACT

An air massage device which allows for a uniform massage treatment upon a human body. This is accomplished by having a person lie upon an air-mat divided into three distinct sections, with each section corresponding to either the upper, middle or lower region of the human body. Within the upper and middle sections are a plurality of air-bags which can be inflated and deflated independently of each other. In order to massage one of the regions of the human body lying upon the mat, the air-bags within one of the mat sections are inflated and deflated in such a sequence that an inflation/deflation frequency of all the air-bags contained within that section of the air-mat will be equal over any set period of time. In this manner, a uniform massage is assured as each air-bag within the section will inflate and deflate an equal number of times.

6 Claims, 6 Drawing Sheets

AIR MASSAGE DEVICE

CROSS REFERENCE TO RELATED APPLICATIONS

This is a continuation-in-part application consolidating U.S. application Ser. Nos. 08/212 957, 08/212 956 and 08/212 959, all filed on Mar. 15, 1994 and all now abandoned.

BACKGROUND OF THE INVENTION

1. Field of the Invention

This invention relates to an air-massage device equipped with an inflatable air-mat. A human body can receive a massage treatment by lying on the mat, which is divided into three specific regions. A first region is designated for neck and shoulder areas of a person, a second region is designated for the waist, and a third region is designated for the lower extremities or legs. Within each of the three regions of the air-mat are installed a number of individual air-bags which can be inflated and deflated independently of each other.

2. Description of the Prior Art

Previously invented air-mat devices, such as Japanese Utility Model Publication No. 10994 (1991), are constructed so that a number of air-bags are installed in the body of the mat, and a human body lying on the mat can be massaged by independently inflating and deflating some of the air-bags by means of an intake/exhaust instrument installed within the air-mat device.

In addition, air-massage devices equipped with an air-mat divided into sections for the upper, middle and lower regions of the human body and provided with air-bags within each of these regions are known and currently used in the field.

These previous air-massage devices were designed to provide repeated massage therapy on a selected region of a human body by expanding and contracting the air-bags within a specified region. The air-bags are first expanded and contracted in a regular sequential order. Then, when the last air-bag at one end of the specified region has been expanded and contracted, the sequential order is reversed, so that the next to last air-bag will expand and contract, and then the second to last air-bag will expand and contract, etc. so that the expansion and contraction of each of the air-bags will proceed in an opposite direction.

Previous air-massage devices provide non-uniform massage treatments due to their method of expanding and contracting the air-bags within a specified region to be treated. Specifically, the air-bags of a prior art device are expanded and contracted in a regular order. When the last air-bag at the end of the specified region has been expanded and contracted, the expansion/contraction order is reversed so that the next to last air-bag will be the first air-bag to be expanded and contracted in the new reverse order. However, in such a method, the expansion/contraction frequency of the air-bags at the ends of the specified region will tend to be lower than the expansion/contraction frequency of the air-bags located inbetween the two end air-bags. For example, if a specified region of an air-mat contained three air-bags, A, B and C, the expansion and contraction of each of these air-bags would proceed in the following order:

A→B→C→B→A→B→C→B→A

Accordingly, during any one set period of time, the A air-bag is expanded/contracted three times, or has a frequency of three, while air-bag B has a frequency of four and air-bag C has a frequency of two. As one can observe, each air-bag within the specified region is expanded and contracted an unequal number of times compared to the other air-bags. As a result, the prior art massage device will provide an uneven or non-uniform massage.

Further, it was very troublesome to use the previously invented air-mat devices, as the body of the mat is covered with a material that is the same or similar to the material used to make the mat. Accordingly, the mat had to be used in conjunction with a separate cover, such as a blanket in the winter and a straw mat in the summer.

However, the use of a cover, such as a blanket or straw mat, upon the air-mat reduces the effectiveness of the massage treatment upon a human body lying on the mat as the cover impedes the massage effect produced by expansion and contraction of the air-bags within the mat.

Still further, in the previous air-bag devices, difficulties arise in determining the position of a human body lying on the body of the mat relative to the air-bags as the process of inflating and deflating the air-bags begins once the instrument has been turned on.

SUMMARY OF THE INVENTION

The current invention improves on the problem discussed above by providing an air-massage device which is capable of providing a uniform massage treatment over a selected region of the human body.

An air-massage device is equipped with an air-mat. The air-mat is formed into three sections, i.e. a first section for the neck and shoulder region of the human body, a second section for the waist region, and a third section for the leg region. Within each of the sections are a plurality of air-bags. The body of the air-mat is then covered with a heat-trapping blanket on one side, and an air-permeable cotton on the other side. With this construction, an operator can select the type of air-mat surface desired by simply selecting which side of the air mat to lie on. By selecting the heat-trapping blanket as the surface for relatively colder seasons, such as winter, and the air-permeable cotton surface for relatively warmer seasons, such as summer, the user can attain greater comfort and rest easier upon the mat.

The air-massage device also includes an intake/exhaust instrument which is used to supply air to these air-bags, thereby expanding and contracting them so as to provide a massage treatment to a human body lying upon the mat. Additionally, when a particular region of the human body is designated to receive massage therapy, the air-bags within a particular section of the mat will expand and contract in a regular order in such a way that the expansion/contraction frequency of all the air-bags will be equal, thereby providing a uniform massage treatment. Specifically, an equal expansion/contraction frequency among the air-bags is assured by expanding and contracting the air-bags within the designated section in such a manner that the air-bags located at either end of the air-mat section will be expanded and contracted two consecutive times before any of the air-bags inbetween the end air-bags are expanded and contracted during a reversal of the expansion/contraction order.

In order to further improve on the above difficulties, the air-mat device is installed with several air-bags which are capable of being selected by an intake/exhaust instrument and individually supplied with air, thereby inflating any one of the individual air-bags and providing pressure upon a localized area of the human body lying on the mat. In a first embodiment, one of the several air-bags is arranged at a position that corresponds to the neck region of the human body lying on the mat, and only this air-bag is expanded and contracted for a fixed duration of time during the initial operation of the intake/exhaust instrument.

The determination of the relative position of the human body to the mat is then simplified, as only the air-bag arranged at the neck position of the human body is expanded and contracted during the first initial moments when the intake/exhaust instrument is activated.

In a second embodiment, one of the several air-bags is arranged at a position that corresponds to the waist region of the human body. Then similarly to the first embodiment, this individual air-bag is expanded and contracted for a fixed duration of time during the initial operation of the intake/exhaust instrument.

Similar to the first embodiment, the determination of the relative position of the human body to the mat is simplified in the second embodiment as only the air-bag arranged at the waist position of the human body is expanded and contracted during the first initial moments when the intake/exhaust instrument is activated.

As either the neck or waist of the user should then be properly positioned upon the mat, variations in the effectiveness of the massage treatment due to differences in human stature are minimized.

DETAILED DESCRIPTION OF THE INVENTION

All examples of the invention below are in reference to FIGS. 1–9 described earlier. Note that terms in quotation marks "" represent functional modes of the air-mat device while terms contained in brackets [] represent indicators found on the air-mat device.

Figure 1:
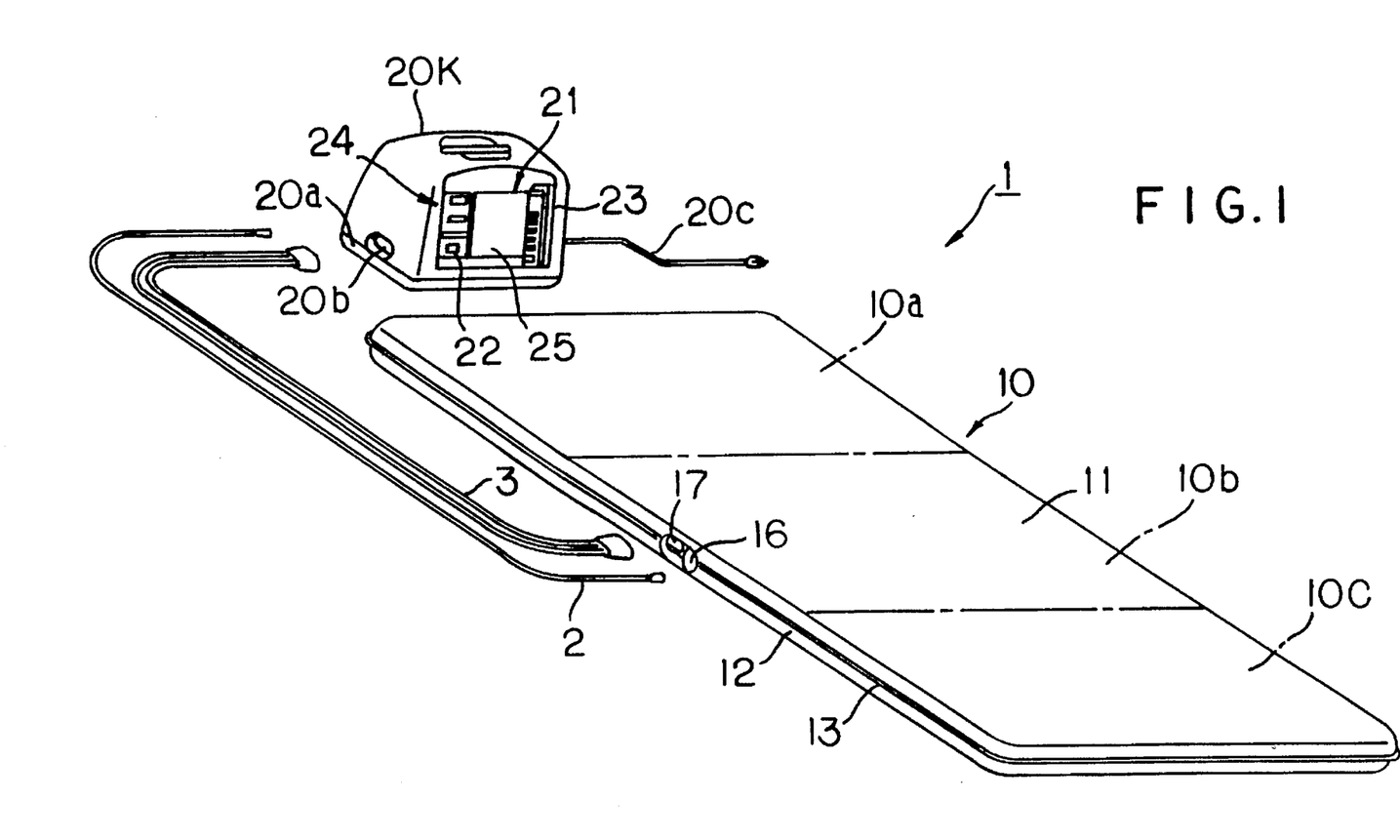
FIG. 1 depicts a perspective view of the total air-mat device.

As shown in FIG. 1, the air-mat device 1 is comprised of the air-mat 10, which has a defined depth, along with the device body 20, which contains an intake/exhaust instrument. The air-mat and device body are connected to each other by means of a wiring cable 2 and a hose bundle 3, which comprises a plurality of parallel air hoses bundled together.

Figure 2:
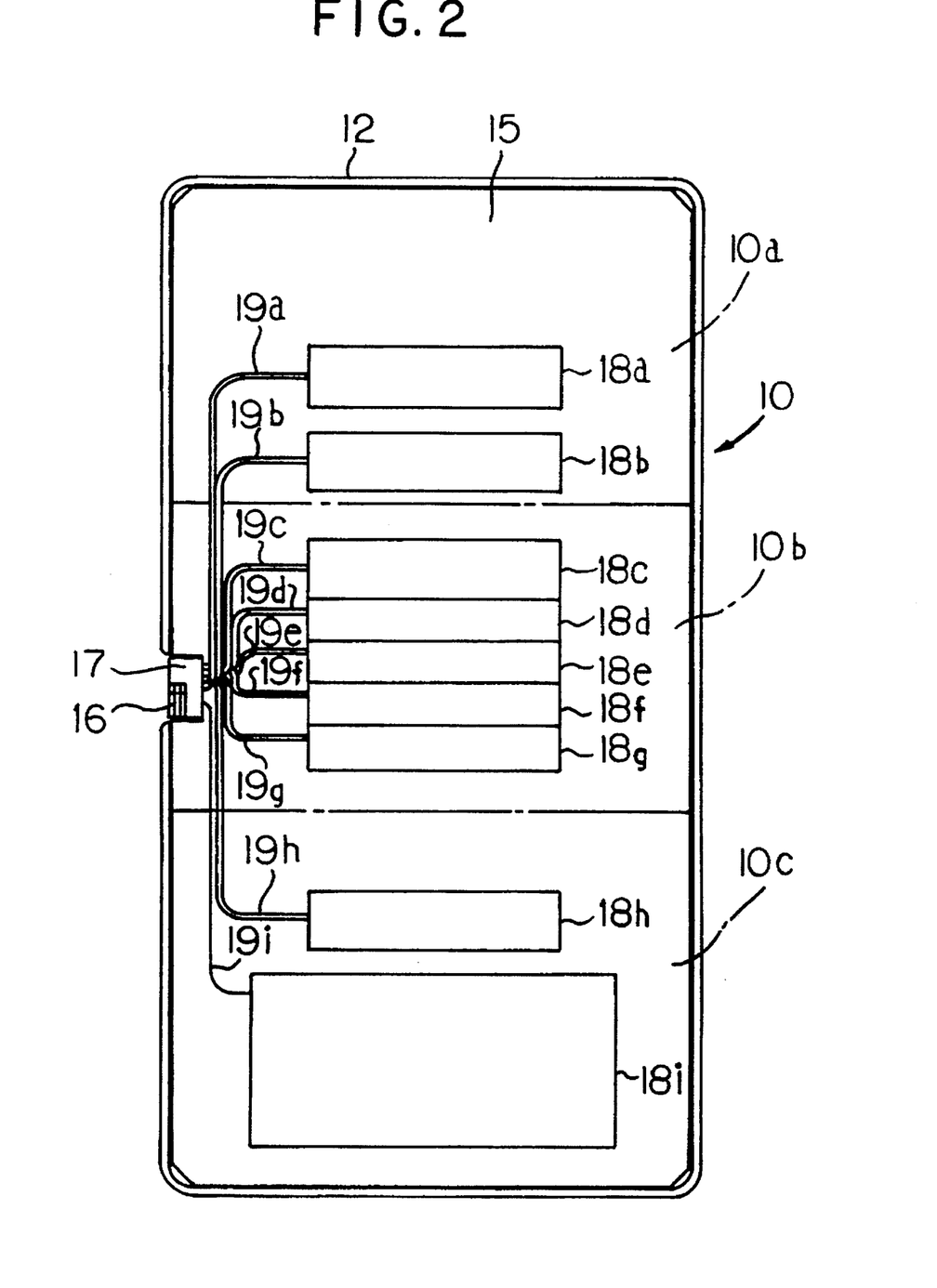
FIG. 2 depicts a plane view of the air-mat itself.
Figure 3:
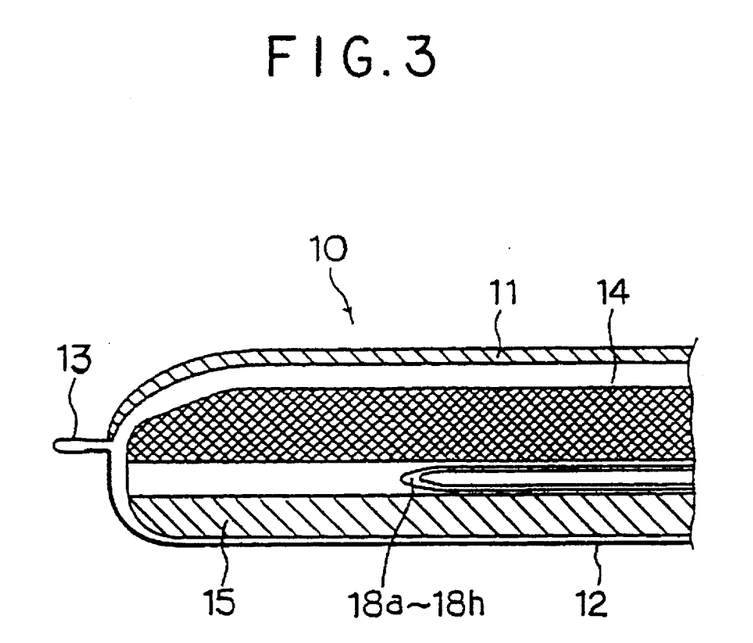
FIG. 3 depicts a longitudinal section of the air-mat and its construction.

FIGS. 1 and 2 further depict the air-mat upon which a human body would lie wherein the air-mat is divided into three regions, i.e. a neck-and-shoulder region 10a, a waist region 10b, and a leg receptive region 10c. As depicted in FIG. 3, the air-mat itself 10 has an upper part or pad 14 and an underside or pad 15, both made of polyurethane. A first side of the mat is covered with a cloth surface 11 made of nap-raising polyester, and a second side of the mat is covered with a lining cloth 12 made of cotton. Both covers are attached to the edge of the mat by either sewing them at the hems or fastening them with hem-stoppers 13. To provide comfort regardless of the season, it is suggested that cover 11 be used as the surface during the winter, and cover 12 as the surface during the summer. Additionally, the polyurethane pads 14 and 15 are set inside the body of the mat so to provide cushioning.

Oblong air-bags 18a–18h are installed within the mat, between the upper part 14 and underside 15. Air-bags 18a and 18b are installed at the neck-and-shoulder region 10a, air-bags 18c–18g at the waist region 10b, and air-bag 18h at the leg region 10c. An electric plate 18i is installed inbetween the upper part 14 and underside 15 at the leg region 10c.

A hose connection device 17 is provided at one side of the air-mat 10, and is connected to the air-bags 18a–18h by way of tubes 19a–19h. Further, connection part 16 is provided near the hose connection device 17, and is connected to a leading wire 19i connected to electric plate 18i.

One end of hose bundle 3, which is composed of several tubes, is removably connected to the hose connective device 17. The other end of hose 3 is removably connected to case 20k of the main operation control unit, within which is installed the intake/exhaust instrument 20 (see FIG. 5). More particularly, wiring cable 2 and hose bundle 3, at their ends opposite of the mat, contain connection parts 20a and 20b, respectively, which connect to one side of device 20. A wiring cord 20c for supplying electricity connects to the other side of device 20.

By connecting hose 3 with both the case 20k of the main control unit and with the hose connection part 17 of the air-mat 10, air can be independently supplied to each of the air-bags 18a–18h with the aid of the intake/exhaust instrument 20. The expansion and contraction of each of the air-bags 18a–18h, produced by the supply and removal of air from the instrument 20, causes the rising and lowering of upper part 14 of mat 10, thereby resulting in a massage treatment to a human body lying upon the mat.

Figure 4:
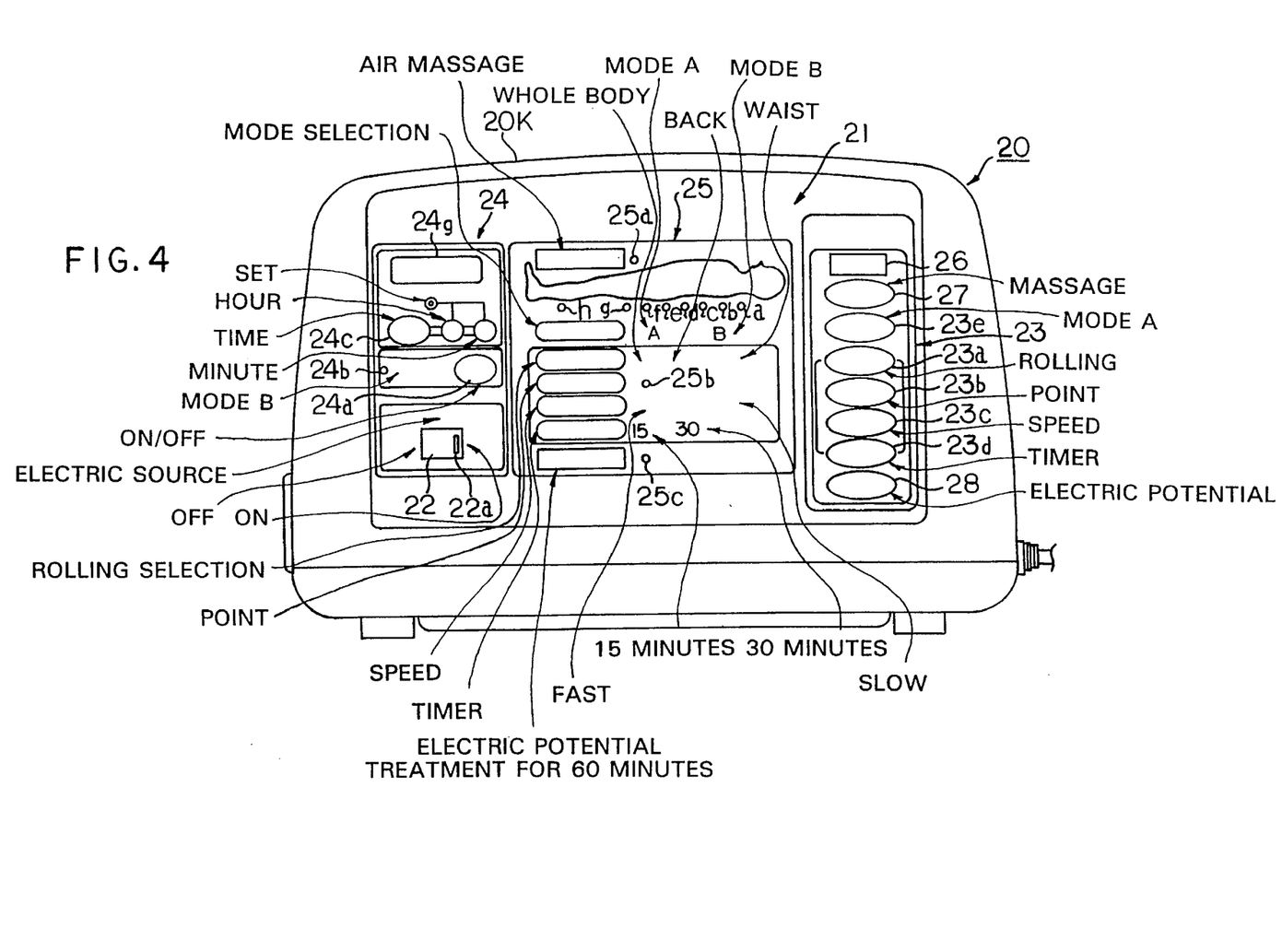
FIG. 4 depicts a plane view of the operational panel, including the arrangement of switches.

An operation panel 21, which is placed at the front of case 20k of the main control unit containing the intake/exhaust instrument 20, contains a switch 22 for an electric source, an operation part 23, an alarm-setting part 24 and a display part 25 for indicating the various operating states and set-up modes, as shown in FIG. 4.

The power supply to the operation panel 21 is controlled by electric source 22. When electric source 22 is in an ON position, the luminous body 22a of a luminescent diode is lit.

Set within the operation part 23 are numerous controls, including rolling switch 23a, which selects whether the whole body, back or waist is to be massaged. Point selection switch 23b selects one of the air-bags 18a–18h, allowing a massage treatment upon a localized part of the human body. Speed selection switch 23c regulates the speed of expansion and contraction of air-bags 18a–18h. Timer switch 23d sets the operation period of the massage device. Typically, these rates will be categorized as either "fast" or "slow". Switch 23e is used for selecting a mode A which allows a user to sleep upon the device. Switch 27 selects an air-massage treatment, and switch 28 selects the electric potential treatment by electric plate 18i. Additionally, an optical receptor 26, which receives infrared light produced by a remote-control (not shown) is fixed upon operation part 23.

Switch 24a is used for selecting a mode B. A time setting switch 24 is then used to set a wake-up time which activates an alarm bell, and a display section 24g, which indicates the present time, are both located within setting part 24. Selecting the course B operating state by means of the course B switch 24a, activates the timer function, the timer-setting switch 24c, the time-setting switches 24d and 24e used to set the hour and minute and an execution switch 24f for placing the set time into memory. When mode B has been selected, a luminous diode 24b is lit.

On the display panel 25 are contained a luminous diode 25a, which is lit when switch 27 for turning on the air massage is activated, a luminous diode 25b, which is lit when switch 23b for point selection has been activated, and luminous diode 25c, which is lit when switch 28 for turning on the electric potential treatment has been activated. Additionally located upon the display panel are luminous diodes a–h, which represent the individual air-bags 18a–18h, respectively. Luminous diodes a–h are lit in relation to the expansion of air-bags 18a–18h, respectively. In addition, diodes a–h are lit in regular order every time the point selection switch 23b is activated, and whenever one of the air-bags 18a–18h corresponding to one of the luminous diodes a–h is selected, those selected bags are exclusively expanded and contracted.

On the remote control apparatus (not shown), switches having similar functions to those quipped on the operation panel 21 are provided. With these switches on the remote control apparatus, it is possible to do the same operations as those with the switches on the operation panel 21.

Figure 5:
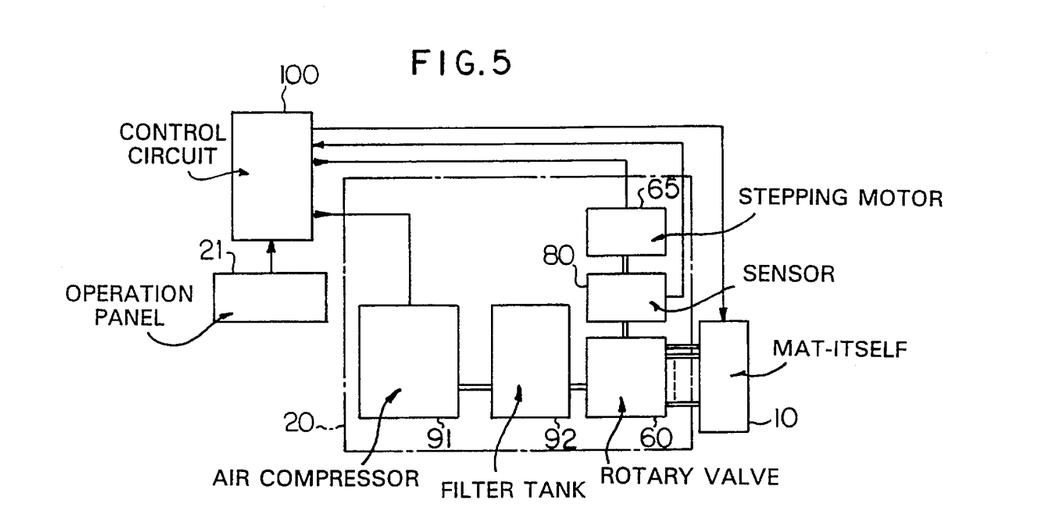
FIG. 5 depicts a block diagram showing an approximate construction of the air-massage device of this invention.
Figure 6:
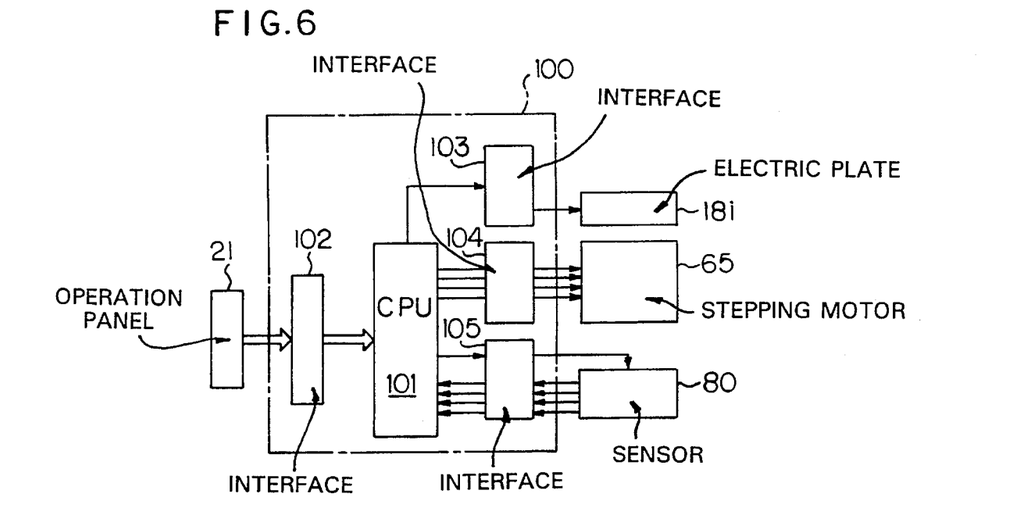
FIG. 6 depicts a block diagram showing the construction of a control unit of the air-massage device.

The case 20k for the main control part contains a built-in rotary valve 60, which has a rotor (not shown) rotated by a stepping motor 65, as shown in FIG. 5. At any one time, one of the air-bags 18a–18h is connected to a filter tank 92, while the disconnected bags are kept under atmospheric pressure. Thus, for example, when air-bag 18a is connected to filter tank 92, compressed air is supplied solely to air-bag 18a, which is expanded, while the other bags 18b–18h are not expanded but instead kept under a pressure equal to that of the atmosphere.

As the valve rotor is rotated, the air-bag 18b is connected to the filter tank 92 and only this bag is expanded while the remaining bags 18a and 18c–18h are kept under an atmospheric pressure. Thus the rotary valve 60 changes the air-bags 18a–18h to be connected to the filter tank 92 one by one in a regular order in the course of rotation of the rotor.

This rotary valve 60 is constructed in such a way that, when the rotor has stopped at a middle point where none of the air-bags are connected to the filter tank 92, all of the air-bags 18a–18h are kept under an atmospheric pressure. Beside the rotary valve 60, a sensor 80 is arranged for detecting which one of the air-bags 18a–18h is connected to the filter tank 92.

A air-compressor 91 is used to produce compressed air, while the filter tank 92 purifies and stores the compressed air. These are both installed in case 20k of the main control.

Additionally provided is a control circuit 100 (control system) for controlling the stepping motor 65, electric plate 18i, etc. based on the operation of each switch upon the operation panel 21. The control circuit 100, which is installed within case 20k, is constructed from a microcomputer 101 and interfaces elements 102–105 as shown in FIG. 5.

OPERATING STATES

The various operating states of the air-mat instrument are explained below.

Air-Massage/Course A

In the Course A operating state, the expansion or contraction of the air-bags 18a–18h proceed by the work of the intake/exhaust instrument after a predetermined operation. First, the electric source 22 and then the air-massage switch 27 should be turned to "ON".

Furthermore, in this instance, the speed of expansion or contraction of the air-bags 18a–18h should be set to "fast", the timer to "15 min" and the rolling mode to "full body".

Under these conditions, the luminous bodies 22a and 25a are respectively lit to indicate the "ON" status of switches 22 and 27. The luminous body 22a remains lit until the electric source 22 has been switched to the ([OFF]) position.

Initially, only the air-bag 18a is expanded and contracted by intaking and exhausting air to and from the air-bag 18a, which is arranged at the position corresponding to the neck of the human body lying on the mat. This automatic selection of air-bag 18a by the intake/exhaust instrument is done to determine the position of the human body relative to the mat 10. Under these conditions, the luminous body 25b, luminous body a, and the signals [fast] and [15 min] are either set on or off.

The relative position of the human body to the mat 10 can also be determined by use of air-bag 18d, which is arranged at the position corresponding to the waist of the human body lying on the mat. This is done by repeating the expansion and contraction of air-bag 18d at an appointed time by supplying air from the intake/exhaust instrument into the air-bag 18d.

At this time, the luminous body d, not luminous body a, is lit on and off. It is noted that the determination of the relative position of the human body by expanding and contracting air-bag 18d, which is arranged at the area corresponding to the waist of the human body, can be more accurate than a determination made by expanding and contracting air-bag 18a, which is arranged at the area corresponding to the neck of the human body.

After the position of the human body relative to the mat 10 has been determined, if the course A switch 23e is pressed, the air-bags 18a–18e will be expanded and contracted in order by air provided by the intake/exhaust instrument and supplied by the hose bundle 3 and inner hoses 19a–19h, thereby providing a massage treatment to the lying body (for example, from the lower legs toward the neck) as will be described more fully herein. After 15 minutes, the operation of the intake/exhaust instrument will stop automatically.

Under these operating conditions, the indicators showing [Course A], [full body], [fast] and [15 min.] on the display panel will be lit. Additionally, the luminous bodies a–h will light with the expansion of their corresponding air-bags 18a–18h.

Air Massage/Course B

The course B operating state is used in order to make the expansion and contraction of air-bags 18a–18h start, by the work of the intake/exhaust instrument, either after a prescribed usual operational time or at a determined time. First, the electric source 22, and then the course B switch 24a, are turned on. Furthermore, in this initial mode, the speed of expansion and contraction of the air-bags should be set to "fast, the timer to "15 min", and the rolling mode to "full body".

Under these conditions, the luminous bodies 22a and 24b will, respectively, be lit to indicate the operation of switches 22 and 24a. Luminous body 22a remains lit until the electric source 22 is switched to the "OFF" position.

Next, the starting time of operation is set by the time setting switches 24d and 24e, which are located beneath the timer setting switch 24c. The time display 24g can be used to confirm the time set.

When the execution starting time has arrived, air-bags 18a–18h are expanded and contracted in order by air supplied by the intake/exhaust instrument and provided through the hose part 3 and inner hoses 19a–19h. This provides a massage treatment to the lying body. After 15 minutes, the operation of the intake/exhaust instrument stops automatically.

Under these operating conditions, the luminous bodies 22a and 24b, along with the indicators upon the display panel showing [Course A], [full body], [fast] and [15 min.], are lit. Additionally, the luminous bodies a–h will light with the expansion of their corresponding air-bags 18a–18h.

When the execution starting time arrives, the user can be alerted by means of a buzzer before the intake/exhaust instrument actually activates. In the course A operating state, the massage action will begin after the position of the human body relative to the mat has been determined by expansion and contraction of air-bags 18a and 18d, which are arranged respectively at the areas corresponding to the neck and waist of the lying body.

By the way, it is possible to operate in the course A state and course B state at the same time. Additionally, in the embodiment above, the speed of expansion/contraction of the air-bags was set to "fast", the timer to "15 min", and the rolling mode to "full body". However, different selections and combinations of these modes are available and left to the option of the user.

Electric Potential Treatment

When treatment with an electric potential by means of the electric plate 18i is desired, the electric source 22, and then the electric potential treatment switch 28, must be placed in the "ON" position. After treatment with the electric plate 18i has begun, it can be automatically stopped with the passage of a prescribed amount of time, for example, 60 min.

Under these operating conditions, luminous bodies 22a and 25c will be lit to indicate the operation of switches 22 and 28. Additionally, luminous body 22a remains lit until the electric source 22 has been switched to the "OFF" position.

When it is desired to stop the electric potential during the middle of the treatment, one only has to place the electric potential treatment switch 28 to the "OFF" position. When an air-massage treatment is desired, it is easy to change the operating mode by placing any one of the air-massage switch 27, course A switch 23e, rolling mode switch 23a, and point mode switch 23b to the "ON" position.

When an electric potential treatment is desired after completing an air-massage, and the electric potential treatment switch 28 has been left in the "ON" position while executing the air-massage, the device will remain in a reserved condition for providing an electric potential treatment. When luminous body 25c turns off, the air-massage has stopped and the electric potential treatment will be initiated by the electric plate 18i. To indicate this, the luminous body 25c will be lit.

The air-mat device of this invention, constructed as mentioned above, can easily determine the position of the lying human body to be treated relative to the air-bags. Accordingly, an effective healing treatment can be provided for any user.

INFLATION SEQUENCE

Use of the air-massage device mentioned above is further explained below by means of examples.

First, switch 22 on the operation panel 21, for turning the electric power on and off, is activated.

Next, massage switch 27 is activated after the part of the body to be massaged, for example, the back, has been selected by rolling switch 23a. Then, the control circuit 100 causes the stepping motor 65 to function and the compressor to start, in order to accumulate compressed air in the filter tank 92.

Figure 7:
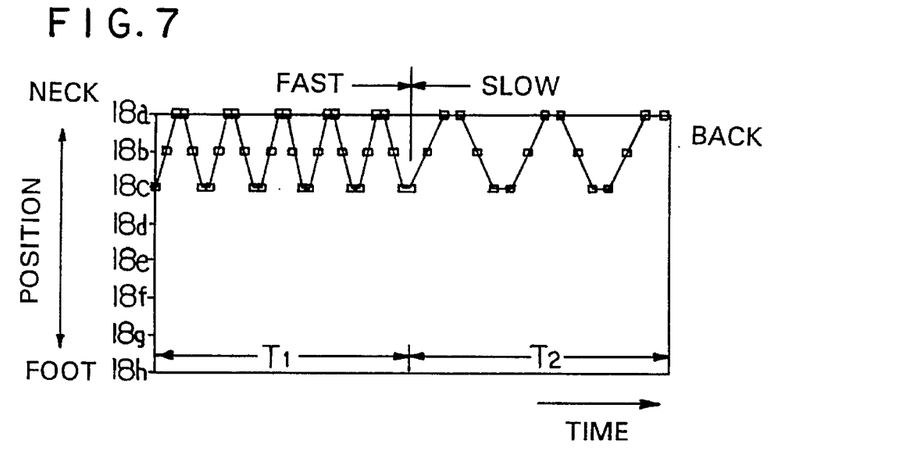
FIG. 7 depicts a time-chart representation of the expansion and contraction of the air-bags against the back of a human body.

As shown in FIG. 7, the air-bags are expanded and contracted in the order of 18c, 18b and 18a under the control of the stepping motor 65. Yet after two consecutive expansions and contractions of the air-bag 18a, the air-bags are expanded and contracted in the reverse order 18a, 18b and 18c. But after two consecutive times of expansion and contraction of the air-bag 18c, the air-bags are again expanded and contracted in the initial order 18c, 18b, 18a. These mechanical movements are repeated several times in a time period of T1.

In a time period T2, the same mechanical movements as those in T1 are repeated, and hence, the massage treatment over the back of the human body is repeated in a period of T1 plus T2. The time T2 for expansions and contractions is usually set up to be longer in duration than the time period T1.

During the sequential expansion and contraction of air-bags 18a, 18b and 18c as described above, air-bags 18a and 18c, which are located at either end of the back region, are expanded and contracted two consecutive times during the reversal of the expansion/contraction order. As a result, a specific pattern is observed during the specified order of expansion/contraction of air-bags 18a–18c during the time period T1+T2. This specific pattern is as follows: 18c, 18b, 18a, 18a, 18b, 18c, 18c, 18b, 18a, 18a, 18b, 18c. Due to this reversal of expansion/contraction order, where the end air-bags are inflated two consecutive times, the expansion and contraction frequency of each air-bag is four. Specifically, for the above expansion/contraction sequence, air-bag 18a, 18b and 18c are all inflated/deflated exactly four times. Due to this specific inflation sequence where each individual air-bag is guaranteed to be inflated/deflated an equal number of times as every other air-bag in the defined region, it is possible to provide a uniform massage treatment upon the specified body region (i.e. back region).

Figure 8:
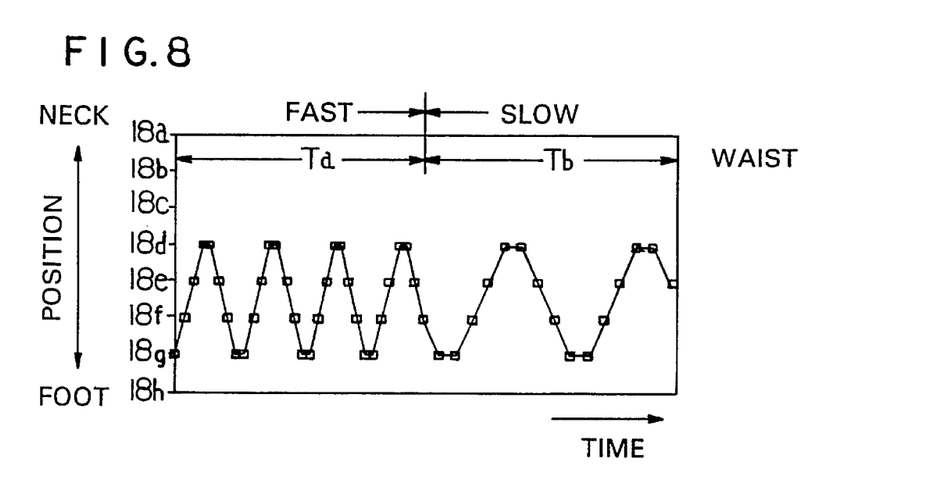
FIG. 8 depicts a time-chart representation of the expansion and contraction of air-bags against the waist of a human body.

As a next example, as shown in FIG. 8, when the massage switch 27 is activated after the selection of "waist" by the rolling selection switch 23a, the air-bags 18g–18d are expanded and contracted in the following order: 18g, 18f, 18e and 18d. Then, after it has been determined that the air-bag 18d has been expanded and contracted two consecutive times, the air-bags are expanded and contracted in the reverse order from 18d to 18g. Then, after it has been determined that air-bag 18g has been expanded and contracted two consecutive times, the air-bags are again expanded and contracted in the initial order, from 18g to 18d. This process is repeated several times over a time period of Ta.

In a time period of Tb, the same expansion and contraction process as that in Ta are repeated, and hence, the massage treatment over the waist region is repeated over a period of Ta plus Tb. The duration of time for Tb is usually greater than that for Ta.

During the sequential expansion and contraction of air-bags 18d, 18e, 18f and 18g as described above, air-bags 18d and 18g, which are located at either end of the waist region, are expanded and contracted two consecutive times during the reversal of the expansion/contraction order. As a result, a specific pattern is observed during the specified order of expansion/contraction of air-bags 18d–18g during the time period Ta+Tb. This specific pattern is as follows: 18g, 18f, 18e, 18d, 18d, 18e, 18f, 18g, 18g, 18f, 18e, 18d. Due to this reversal of the expansion/contraction order, where the end air-bags 18d and 18g are inflated two consecutive times, the expansion and contraction frequency of each air-bag is three. Specifically, for the above expansion/contraction sequence, air-bags 18d, 18e, 18f and 18g are all inflated/deflated exactly three times. Due to this specific inflation sequence where each individual air-bag is guaranteed to be inflated/ deflated an equal number of times as every other air-bag in the defined region, it is possible to provide a massage treatment upon the specified body region (i.e. waist region) which will be uniform.

Figure 9:
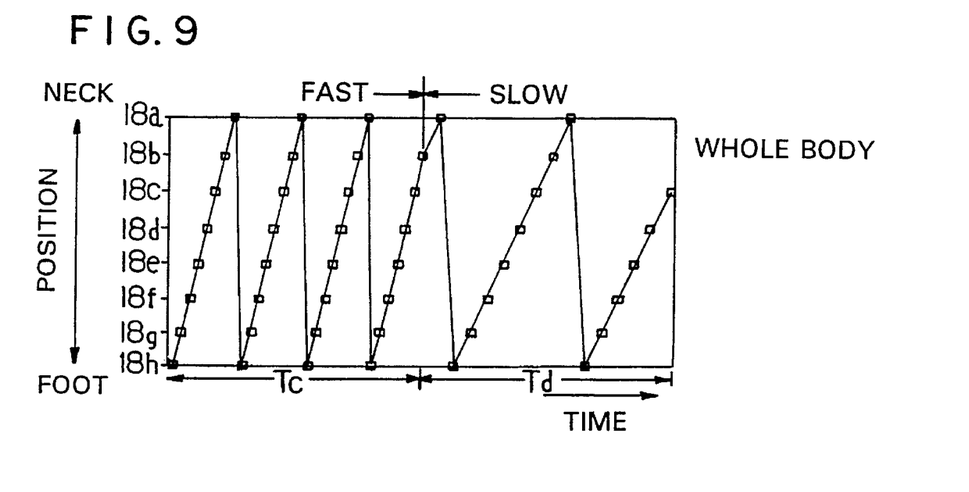
FIG. 9 depicts a time-chart representation of the expansion and contraction of air-bags in the case of a total body massage.

Next, as shown in FIG. 9, when the massage treatment switch 27 is activated after the selection of "whole body" by the rolling selection switch 23a, the air-bags 18h–18a are expanded and contracted in the reverse alphabetical order (i.e. 18h, 18g, 18f, . . . 18a). Then, after it has been determined that air-bag 18a has been expanded and contracted two consecutive times, the air-bags are expanded and contracted in the regular alphabetical order (i.e. 18a, 18b, 18c, . . . 18h). After it has been determined that air-bag 18h has been expanded and contracted two consecutive times, the air-bags are again expanded and contracted in the initial order, from 18h to 18a. This process is repeated several times over a time period of Tc. Likewise, in a time period of Td, the same expansion and contraction process as that in Tc are repeated, and hence, the massage treatment over the entire body, which will be repeated over a period of Tc plus Td, will be uniform as each air-bag will have an inflation/ deflation frequency identical to every other air-bag. Note that the duration of time for Td is usually greater than that for Tc.

In order to perform an electric potential treatment, a switch 28 for electric potential treatment is activated, then the electric potential of 100 volts is imposed on the electric plate 18i by means of the control circuit 100, thereby initiating an electric potential treatment. The period of time for which the electric potential treatment lasts is fixed at 60 minutes.

As explained above, by selecting the air-bags located at both ends of a region specified to receive a massage treatment, and expanding and contracting these specific air-bags two consecutive times during the normal expansion/contraction order of all the air-bags within the specified region, it can be assured that each of the air-bags within the region will be expanded/contracted an equal number of times, thereby providing a uniform massage treatment to the selected region of the human body.

Accordingly, a human body can lie upon the air-mat and receive a therapeutic massage treatment by operating the air-mat device in various operating states. Additionally, the body of the air-mat is covered with a first type of material on a first side, and a second type of material on a second side. The material on one side is designed to function as a heat-trapping cover, while the material on the opposite side functions as an air-permeable cover. Then, by flipping the mat over onto its first or second side, the user can lie either upon the heat-trapping or air-permeable covered side, thereby receiving the greatest comfort relative to the seasonal weather and climate conditions. As no separate cover, such as a blanket or straw mat, need be thrown upon the air-mat, no additional layers of material will come between the air-mat and user, thereby assuring that he or she will receive the maximum effect of the massage treatment.

The embodiments of the invention in which an exclusive property or privilege is claimed are defined as follows:

1. A massage device for providing a uniform massage treatment upon a human body, comprising:

an air-mat divided into three distinct sections and upon which said human body will lie;

a plurality of air-bags installed inside said air-mat so as to be disposed in said three distinct sections of said air-mat;

an intake/exhaust instrument capable of independently supplying air to each individual air-bag of said plurality of air-bags in said air-mat to inflate and deflate said individual air-bags in said air-mat so as to provide said massage treatment upon said human body;

control circuit means for determining which said individual air-bag of said plurality of air-bags in said air-mat will be inflated and deflated with air by said intake/exhaust instrument;

selection means for selecting at least one of a plurality of massage regions of said air-mat for inflation and deflation of said individual air-bag therein to provide said massage treatment, a first one of said massage regions having said individual air-bags therein disposed in two adjacent sections of said three distinct sections; and said control circuit means also including means for causing said individual air-bags within said at least one massage region over a set period of time to be inflated and deflated in an initial successive order, and upon inflation and deflation of a last said air-bag at one end of said initial successive order, for causing each of said individual air-bags of said at least one massage region to then be inflated and deflated in a reverse successive order relative to said initial successive order so that a first air-bag to be inflated and deflated in said reverse successive order is said last air-bag to be inflated and deflated during said initial successive order, each said air-bag being substantially deflated after being inflated before a next successive one of said air-bags is inflated, wherein said individual air-bags in said first massage region are successively inflated and deflated between said two adjacent sections when said first massage region is selected by said selection means.

2. A massage device according to claim 1, in which said air-mat includes first and second outer sides which define opposite sides of said air-mat, a heat-trapping material being attached to and covering said first outer side of said air-mat and an air-permeable material being attached to and covering said second outer side of said air-mat.

3. The massage device according to claim 1, wherein one said air-bag is arranged at a position corresponding to a waist region of said human body lying on said air-mat, said control circuit means further including means for permitting only said one air bag to be inflated and deflated within a set period of time during an initial operating condition of said intake/exhaust instrument, thereby allowing a relative position of said human body to said air-mat to be properly adjusted.

4. The massage device according to claim 1, wherein one said air-bag is arranged at a position corresponding to a neck region of said human body lying on said air-mat, said control circuit means further including means for permitting only said one air bag to be inflated and deflated within a set period of time during an initial operating condition of said intake/exhaust instrument, thereby allowing a relative position of said human body to said air-mat to be properly adjusted.

5. A massage device according to claim 1, wherein one of said air-bags is a positioning air-bag disposed at a position corresponding to one of a waist region or a neck region of said human body lying on said air-mat, said control circuit means further including means for inflating only said positioning air-bag for a set period of time during an initial operating condition for said intake/exhaust instrument prior to a massaging condition of said intake/exhaust instrument.

6. A massage device according to claim 5, in which said air-mat includes first and second outer sides which define opposite sides of said air-mat, a heat-trapping material being attached to and covering said first outer side of said air-mat and an air-permeable material being attached to and covering said second outer side of said air-mat.

* * * * *

UNITED STATES PATENT AND TRADEMARK OFFICE
CERTIFICATE OF CORRECTION

PATENT NO. : 5 611 772
DATED : March 18, 1997
INVENTOR(S) : Shinichiro FUJIMOTO et al It is certified that error appears in the above-indentified patent and that said Letters Patent is hereby corrected as shown below:

Column 10, line 35; change "air-bag" to
---air-bags---.

Signed and Sealed this

Twenty-sixth Day of August, 1997

Attest:

BRUCE LEHMAN

Attesting Officer

Commissioner of Patents and Trademarks